United States Patent [19]

Lenack

[11] 4,136,041

[45] Jan. 23, 1979

[54] PHOSPHOROTHIONATE DERIVATIVES AND THEIR USE IN LUBRICANTS

[75] Inventor: Alain L. P. Lenack, Mont-Saint-Aignan, France

[73] Assignee: Exxon Research & Engineering Co., Florham Park, N.J.

[21] Appl. No.: 805,328

[22] Filed: Jun. 10, 1977

[30] Foreign Application Priority Data

Jun. 11, 1976 [GB] United Kingdom .............. 24300/76

[51] Int. Cl.$^2$ .............................................. C07F 9/21
[52] U.S. Cl. .................................. 252/46.6; 260/936; 252/46.7
[58] Field of Search ........................ 252/46.6; 260/936

[56] References Cited

U.S. PATENT DOCUMENTS

| | | | |
|---|---|---|---|
| 2,826,550 | 3/1958 | McDermott | 252/46.6 |
| 2,865,948 | 12/1958 | Fusco | 260/985 |
| 2,978,479 | 4/1961 | Kayser et al. | 260/985 |
| 3,005,006 | 10/1961 | Millikan et al. | 252/46.6 |
| 3,354,240 | 11/1967 | Pochowicz | 252/46.6 |

FOREIGN PATENT DOCUMENTS

1138815  1/1969  United Kingdom .................... 260/936

OTHER PUBLICATIONS

Imaev, English Translation from "Zhur. Obsh. Khimmii", vol. 35, No. 10, 1965, pp. 1864–1866.
Kadyrova et al., English Translation from "Zhur. Obsh. Khimmii", vol. 41, No. 8, 1971, pp. 1688–1691.

*Primary Examiner*—Anton H. Sutto
*Attorney, Agent, or Firm*—Frank T. Johmann

[57] ABSTRACT

Compounds of the formula:

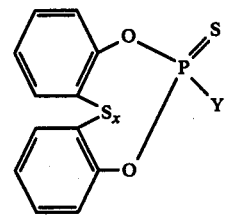

wherein Y is phenoxy, alkylphenoxy, alkoxy, phenylthio, alkylphenylthio, thioalkyl, alkyl or arylamino, and x is 1 or 2, and compounds of the above formula wherein one or both of said aromatic rings are substituted, e.g. with an alkyl group, and their use as antiwear and antioxidant additives in lubricants.

10 Claims, No Drawings

PHOSPHOROTHIONATE DERIVATIVES AND THEIR USE IN LUBRICANTS

The present invention relates to phosphorothionate derivatives of phenol sulfides, particularly alkyl phenol sulphides which are useful as antiwear and antioxidant additives in lubricating oils, the invention also relates to lubricating compositions containing these phosphorothionate derivatives of alkyl phenol sulphides.

Antioxidants are included in lubricating oils to inhibit oxidation of the oil at the temperature at which it is used since oxidation increases the viscosity of the oil rendering it unsuitable as a lubricating oil. Antiwear additives are included to reduce the extent to which the metal parts that are in contact become worn by rubbing against each other. Zinc dithiophosphates are commonly used as both antioxidants and antiwear agents in lubricating oils however these suffer from the disadvantage that they are metal containing and form deposits of what is known as ash. Furthermore there is a tendency away from the inclusion of zinc in lubricants.

There is therefore a need for metal free or ashless antiwear and antioxidant additives for inclusion into lubricating oils. Lubricating additives are usually supplied as concentrates of the additive in oil and so it is important that they have a higher solubility in oil than may be required in the bulk lubricant, which is a drawback of the current ashless antiwear lubricant additive triphenylphosphorothionate. It is also important, especially where the lubricant is to be used as a hydraulic fluid, that the additive be hydrolytically stable.

We have discovered phosphorothionate derivatives of alkyl phenol sulphides and that certain of these materials which are ashless are effective antiwear and antioxidant additives in lubricating oils with sufficient oil solubility to allow them to be supplied as concentrates. Phosphites derived from alkyl phenol sulphides are disclosed in an article in volume 41 No: 8 of Zhurnal Obshchei Khimii at pages 1688 to 1691 and the thiophosphate ionic salts are described in Volume 35 No: 10 of Zhurnal Obshchei Khimii at pages 1864 to 1866 which also describes their use as lubricant additives. Both these classes of materials suffer from the disadvantage that they are not hydrolytically stable. We have found however that our phosphorothionate derivatives have sufficient hydrolytic and thermal stability to allow them to be used as additives in hydraulic fluids.

The present invention therefore provides a compound of the general formula:

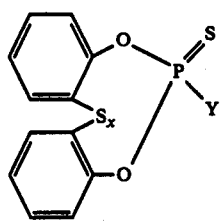

where Y is selected from phenoxy, alkylphenoxy, alkoxy, phenyl thio, alkylphenylthio, thioalkyl, alkyl amino and arylamino, and x is 1 or 2.

The aromatic rings of the compounds of the general formula, including Y when Y contains an aromatic ring, may be substituted. For example, either or both rings may contain a substituent selected from alkyl, nitrogen containing groups, oxygen, sulphur halogen containing groups or halogen itself, carboalkoxy or ether groups. Where the substituents are alkyl we prefer that they contain less than 30 carbon atoms preferably less than 25. Where the compounds are to be used as oil additives the substituent must not of course inhibit the performance of the additive to an undesirable extent. If the compounds are to be used as oil additives we prefer that each aromatic ring of the alkyl phenol sulphide nucleus carries an alkyl substituent containing from 2 to 24 carbon atoms preferably from 6 to 15 carbon atoms since these in which the alkyl substituent contains only 1 carbon atom have limited oil solubility. If Y is aromatic it may also carry such an alkyl substituent. We also prefer that where the compounds are to be used as oil additives the group Y be phenoxy, alkylphenoxy or alkoxy since we find that these compounds tend to have improved oil solubility as compared with the corresponding compounds in which Y is a thio group.

The present invention also provides a process for the production of compounds of the above general formula by first reacting a phenol sulphide, preferably an alkylphenol sulphide, with a phosphorus halide then reacting the product of the first stage with a compound of formula YH where Y is selected from phenoxy, alkyl phenoxy, alkoxy, phenyl thio, alkyl phenyl thio, thioalkyl, alkylamino or arylamino to form the phosphite ester and reacting the phosphite ester with sulphur.

The reaction of the present invention may thus be depicted as follows:

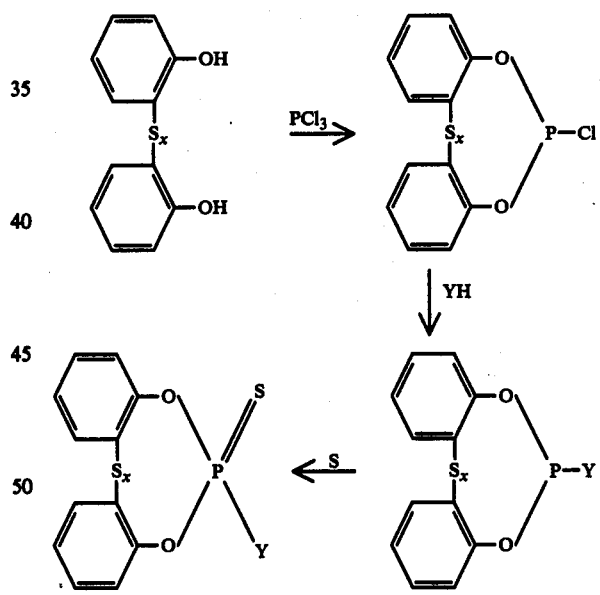

This is however an oversimplification since the final product obtained tends to be a mixture of materials. The exact composition of the mixture and the reason for its formation are not fully understood. Phenol sulphides however tend to be mixtures of compounds containing varying numbers of sulphur atoms in the bridge and also containing polymeric material. Thus where we refer to a value of x in this specification we refer to an average value. Furthermore, where the starting material is an alkyl phenol sulphide it is frequently a mixture of mono- and di-alkyl material.

The reaction of the phenyl sulphide with the phosphorus halide is also thought to give rise to a mixture of products some being cyclic and some being polymeric each containing the repeat units:

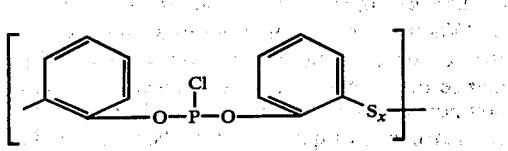

with subsequent reaction with HY and sulphur yielding compounds containing the repeat units:

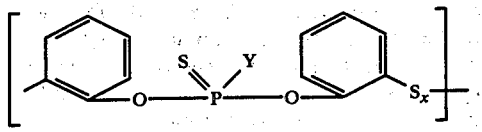

We prefer that a small amount of water be present during the first stage of our process and that a stoichiometric excess of the phosphorous halide be used. Simple monomeric structures are formed when the phosphorous halide reacts with the phenolic groups from the same alkylphenol sulphide molecule whilst polymeric structures are obtained when the phosphorous halide reacts with phenolic hydrogen atoms from different alkyl phenol sulphide molecules. The reaction is preferably carried out in an inert solvent such as toluene and refluxed under an inert atmosphere such as nitrogen.

The reaction of the phosphochloridite derivatives formed in the first stage of our process with the relevant YH compound is preferably carried out in an inert solvent and may be effected in the presence of a base such as an amine for example triethylamine or at high temperatures under an inert atmosphere such as nitrogen. Any suitable solvents may be used and examples include aromatic liquids such as toluene or xylene but where the compounds are to be used as oil additives and are supplied as a solution in a diluent oil we prefer to use the diluent oil as the solvent, this has the added advantage that it is not then necessary to remove the solvent. The triester phosphite produced in the first stage of the process may be converted to the phosphorothionates of the present invention by heating with sulphur, preferably at a temperature in the range 150° C. to 200° C.

As an alternative the compounds of our invention may be prepared by reacting an alkyl phenol sulphide with a phosphorous-thio-halide such as $PSCl_3$. This compound may be reacted with the compound YH or alternatively the stoichiometry may be such that there is excess alkyl phenol sulphide present to provide the compound YH.

As a further alternative the compounds of our invention may be prepared by a process similar to that described in British patent specification No. 1018307 in which phosphorous trichloride, sulphur and the phenol sulphide are reacted in essentially a single stage reaction. This process has the added advantage that lower temperatures may be used. In this process the sulphur, phosphorous trihalide and the phenol sulphide are mixed together and heated to a temperature in the range 50° C. to 150° C. After this reaction is complete the compound YH is added preferably in the presence of a base to remove the hydrochloric acid formed, amines being particularly suitable bases.

The choice of the group Y in the compounds of our invention depends upon the use to which the compounds are to be put. Y should however be selected from phenoxy, alkylphenoxy, alkoxy, phenylthio, alkylphenylthio, thioalkyl, alkyl amino or arylamino and may carry other substituents. Where the materials are to be used as lubricant additives we prefer that Y be alkoxy, phenoxy, or alkylphenoxy, since we find that these materials have the best combination of properties combined with hydrolytic stability. Compounds in which Y is thio-alkyl, phenylthio- or alkylphenylthio also have good antioxidant and antiwear properties but have reduced oil solubility. We also prefer that where the compounds of our invention are to be used as lubricant additives the group Y contain more than one carbon atom since this leads to improved oil solubility. We have found that the compounds of our invention are particularly useful as lubricant additives where they exhibit antioxidant and antiwear properties, they have the advantage of being metal-free and thus ashless, they have improved hydrolytic stability as compared with the earlier proposed phosphites and ionic phosphates and our preferred compounds have improved oil solubility as compared with the currently available ashless antiwear additives.

The compounds of our invention may be used in hydraulic fluids and lubricating oils such as crankcase lubricants for internal combustion engines or metal cutting lubricants. In each instance the compound will generally be used together with other lubricant additives traditionally used in the type of fluid. For example hydraulic fluids generally contain:

Hydrocarbon Oil
Antiwear Additives
Antioxidant Additives
Pour Point Depressants
Antirust Agents and
Antifoam and our compounds may be used as part or all of the antiwear and antioxidant additives whilst crankcase lubricants may contain ashless dispersants such as the polyamine or polyol long chain mono- or di-carboxylic acid or acid anhydride condensation products. They may also contain the overbased metal dispersants such as the high base number calcium and/or magnesium phenates and/or sulphonates. In addition traditional antiwear and antioxidant additives such as the zinc dialkyldithiophosphates may be present although a smaller amount than is traditionally used will be needed due to the presence of the compounds of our invention.

Where the compounds of our invention are used in cutting oils these are usually oil in water emulsions so that the oil will contain an emulsifier which may be an alkylaryl sulphonate, extreme pressure additives will also be present.

The compounds of the present invention may be used in any type of oil which can be animal, vegetable or mineral oil, for example petroleum oil to SAE 30, 40 or 50 lubricating oil grades, castor oil, fish oils or oxidised mineral oil. Alternatively the lubricating oil may be a synthetic ester lubricating oil and these include diesters such as di-octyl adipate, di-octyl sebacate, didecyl azelate, tridecyl adipate, didecyl succinate, didecyl glutarate and mixtures thereof. Alternatively the synthetic ester can be a polyester such as that prepared by reacting polyhydric alcohols such as trimethylolpropane and pentaerythritol with monocarboxylic acids such as butyric acid to give the corresponding tri- and tetra- esters. Also complex esters may be used, such as those formed by esterification reactions between a carboxylic acid, a glycol and an alcohol or a monocarboxylic acid.

The lubricating oil compositions may be concentrates of the compounds of our invention in oil which are supplied for incorporation into bulk lubricating oils or the bulk lubricating oil itself. Where it is a concentrate we prefer that the composition contain from 95% to 60% preferably 90% to 75% by weight of the oil and from 5% to 40% by weight preferably 10% to 25% by weight of the compound of the present invention. Alternatively where the lubricating oil composition is the lubricating oil itself we prefer that the composition contain from 99.99 to 90 preferably 99.9 to 98 wt.% of the oil and from 0.01% to 10% preferably 0.1 to 2% by weight of the compound of the present invention.

The present invention is illustrated but in no way limited by reference to the following Examples.

EXAMPLE 1

563 grams of phosphorous trichloride were added drop by drop to a solution of 1300 grams of a commercially available nonylphenol sulphide in 400 grams of toluene. 2.7 grams of water were added and the solution refluxed for 3 hours under a blanket of nitrogen after which the toluene and excess phosphorous trichloride were removed by vacuum distillation.

Elemental analysis of the product showed carbon 65.0 wt.%, hydrogen 8.4%, sulphur 7.5%, phosphorous 5.9 wt.% and chlorine 7.3 wt.% with a molecular weight of 997. The theoretical content for the compound:

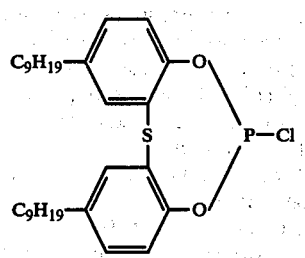

is carbon 67.9 wt.%, hydrogen 8.2 wt.%, sulphur 6.0 wt.%, phosphorous 5.8 wt.% and chlorine 6.6 wt.% with a molecular weight of 534. This therefore indicates the probability of some molecules containing polysulphide linkages and some being polymeric.

66 grams of nonylphenol were dissolved in 90 mls of toluene and 30.3 grams of triethylamine added to this solution. A solution of 160.3 grams of the bis (nonylphenoxy) sulphide phosphorochloridite prepared above dissolved in 250 mls of toluene was added to this nonyl phenol solution held at 40° C. and the resulting mixture stirred for 3 hours and the precipitated triethylamine chlorohydrate filtered off and the toluene removed by vacuum distillation.

Elemental analysis of this product showed it to contain 73.8 wt.% carbon, 9.7 wt.% hydrogen, 5.5 wt.% sulphur, 4.4 wt.% phosphorous and just a trace of chlorine. The molecular weight was 1156.

The theoretical content for the structure:

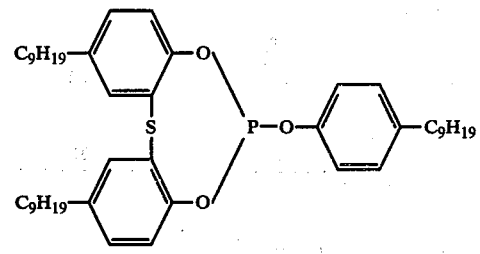

is 75.0 wt.% carbon, 9.6 wt.% hydrogen, 4.4 wt.% sulphur and 4.3 wt.% phosphorous with a molecular weight of 718. Here again indicating the probability of some polysulphide linkages and polymeric molecules.

200 grams of the bis (nonylphenoxy) sulphide nonyl phenoxy phosphite obtained as above were heated with 8.9 grams of sulphur at 190° C. for 30 minutes to yield bis (nonylphenoxy) sulphide nonylphenoxy phosphorothionate.

EXAMPLE 2

The performance of the product of Example 1 as an oil additive was compared with the commercially available antiwear additive triphenyl phosphorothionate (TPPT), 2-nonylphenoxy 1,3,2 benzodioxaphosphole-2-sulphide, bis (nonyl phenoxy) sulphide nonyl phenoxy phosphite and a commercially available zinc dialkyldithiophosphate (ZDDP).

The solubility of the additive in oil was determined by tests conducted on blends of the neat additives in a paraffinic type oil. The blends of additives in oil are made at various concentrations and are stored at room temperature for one week. The values given in Table 1 below are the maximum additive concentrations observed above which a cloudy appearance and precipitate or layering tended to form.

The antiwear properties were assessed by the Hertz 4 ball test (ASTM - 2266) at a concentration of 2.4 milliatoms of phosphorous per 100 grams of oil and the Vickers Vane Pump Test (NF E 48-617) in which the hydraulic fluid is circulated at a pressure of 140 bars, by means of a vane pump (made by vickers, type V.104C) rotating at 1450 r.p.m. The hydraulic fluid is kept at the temperature at which its viscosity is 13 cS and the length of the test is fixed at 250 hours. The pump ring and vanes are weighed before and after the test and the wear, expressed as the weight loss in milligrams. The Hydrolytic Stability of the material is tested according to the test ASTM D-2619.

The results of these tests were as follows:

TABLE 1

| Additive Oil Solubility | TPPT | 2-Nonyl Phenoxy 1,3,2 Benzadioxaphosphate 2-Sulphide | bis (Nonyl-Phenoxy) Sulphide Nonyl-Phenoxy Phosphite | Example 1 | ZDDP |
|---|---|---|---|---|---|
| Oil Solubility Wt.% | 3.5 | 20 | All Propor. | All | All |
| Hydrolytic Stability | | | | | |
| Copper Weight Loss (mg/cm²) | 0.1 | 10 | 1.5 | 0.1 | 0.3 |
| NN on Oil (mg KOH/g) | 0.1 | 0.5 | | 0.1 | 0.3 |
| Acid No. in water phase | 2.7 | 196 | 147 | 16.7 | 4.0 |
| Copper Corrosion | 1A | 4C | 1B | 1B | 2C |

TABLE 1-continued

| Antiwear Properties 4 Ball Data | | | | |
|---|---|---|---|---|
| Scar M.M. | 0.5 | 0.5 | 0.4 | 0.4 |
| Mean Load, Kg | | 34 | 46 | 52 |
| Seizure Load, Kg | | 100 | 126 | 126 |
| Weld Load, Kg | | 160 | 200 | 200 |
| Vickers Vane Pump Test | (2.9) | | (1.2 milli-atoms P per 100 grams oil) | (2.5) |
| (Weight Loss after 250 hours), Mg | | 35 | 41.5 | 66.3 |

EXAMPLE 3

The antioxidancy of the product of Example 1 was measured by the Staeger Oxidation Test (AMS 11 - 32) in which an oil containing 1 wt.% of the product of Example 1 was compared with an oil containing no additive. The acid number of the oil with no additive increased to 0.2 milligrams of KOH per gram in 200 hours whilst that containing the additive required 600 hours for the same increase.

EXAMPLE 4

122 grams of methanol were dissolved in 100 g of toluene and 212 grams of triethylamine added to this solution. A solution of 7288 grams of the bis (nonylphenoxy) sulphide phosphorochloridite prepared in Example 1 dissolved in 400 g of toluene was added to this methanol solution held at 40° C. and the resulting mixture stirred for 3 hours and the precipitated triethylamine chlorohydrate filtered off and the toluene removed by vacuum distillation.

The resulting product has an oil solubility < 2 wt.% as did the product of the reaction of this material with sulphur.

Elemental analysis of the product after reaction with sulphur showed it to contain 12.0 wt.% sulphur, 5.6 wt.% phosphorus and 0.8 wt.% chlorine.

The theoretical content for the structure:

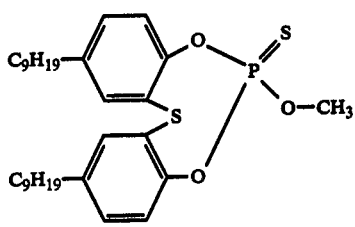

being 11.3 wt.% sulphur and 5.4 wt.% phosphorus.

EXAMPLE 5

282 grams of isobutanol were dissolved in 100 g of toluene and 162 grams of triethylamine added to this solution. A solution of 980 grams of the bis (nonylphenoxy) sulphide phosphorochloridite prepared in Example 1 dissolved in 400 g of toluene was added to this isobutanol solution held at 40° C. and the resulting mixture stirred for 3 hours and the precipitated triethylamine chlorohydrate filtered off and the toluene removed by vacuum distillation. Elemental analysis of this product showed it to contain 5.7 wt.% sulphur, 5.3 wt.% phosphorous and 0.7 wt.% chlorine.

The theoretical content for the structure:

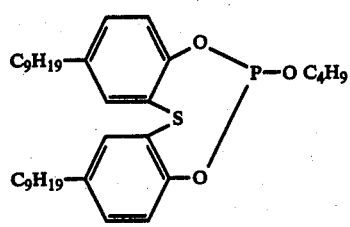

being 5.6 wt.% sulphur and 5.4 wt.% phosphorous.

900 grams of the bis (nonylphenoxy) sulphide isobutoxy phosphite obtained as above were heated with 50.3 grams of sulphur at 190° C. for 30 minutes to yield bis (nonylphenoxy) sulphide isobutoxy phosphorothionate. This product was soluble in amounts greater than 50 wt.% in paraffinic mineral oil.

1.4 wt.% of this material was included in a paraffinic mineral oil containing:

0.4 wt.% of phenolic antioxidant
0.05 wt.% of a dodecyl succinic acid as rust inhibitor and
0.25 wt.% of a copolymeric pour point depressant.

This lubricant which contained 410 parts per million of phosphorous was then subjected to the Vickers Vane Pump Test (NF E 48-617) with the following results:

| Time for Test (hours) | Wt. Loss (milligrams) |
|---|---|
| 25 | 19 |
| 125 | 38 |
| 250 | 51.6 |

EXAMPLE 6

186 grams of phenol were dissolved in 250 g of toluene and 775 grams of triethylamine added to this solution. A solution of 1058 grams of the bis (nonylphenoxy) sulphide phosphorochloridite prepared in Example 1 dissolved in 250 mls of toluene was added to this phenol solution held at 40° C. and the resulting mixture stirred for 3 hours and the precipitated triethylamine chlorohydrate filtered off and the toluene removed by vacuum distillation. Elemental analysis of this product showed it to contain 5.4 wt.% sulphur, 5.5 wt.% phosphorous and 0.6 wt.% chlorine.

The theoretical content for the structure:

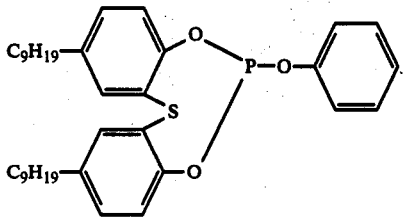

being 5.4 wt.% sulphur and 5.2 wt.% phosphorous.

1000 grams of the bis (nonylphenoxy) sulphide phenoxy phosphite obtained as above were heated with 57 grams of sulphur at 190° C. for 30 minutes to yield bis (nonylphenoxy) sulphide phenoxy phosphorothionate. This product was soluble in amounts greater than 50 wt.% in paraffinic mineral oil.

1.3 wt.% of this material was included in a paraffinic mineral oil containing the same other additives as Example 5 and this oil which contained 440 part per million of phosphorous subjected to the Vickers Vane Pump Test with the following results:

| Time for Test (hours) | Wt. Loss (milligrams) |
|---|---|
| 25 | 3.3 |
| 125 | 7.0 |
| 250 | 30.0 |

The material was also included in a paraffinic mineral oil free of other additives and the oil tested in the Vickers Vane Pump Test with the following results:

| | Treat Rate Wt. % Additive | Time for Test Hours | | |
|---|---|---|---|---|
| | | 25 | 125 | 250 |
| Weight Loss mg. | 1.2 | 201.1 | 36.1 | 46.2 |
| Weight Loss mg. | 1.4 | 14.7 | 41.3 | 73.1 |

EXAMPLE 7

The process of Example 1 was repeated except that the nonyl phenol was replaced with nonyl phenol sulphide to yield a compound whose elemental analysis showed it to contain 3.1 wt.% phosphorous and 0.6 wt.% chlorine. The theoretical content for the compound:

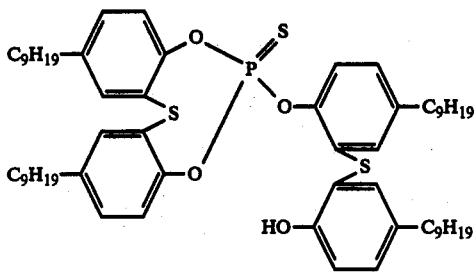

being 3.2 wt.% phosphorous and no chlorine.

The compound was found to be soluble in amounts greater than 50 wt.% in paraffinic mineral oils and two 25 hour trials in the Vickers Vane Pump Test on an oil containing 1.7 wt.% of this material showed 567 and 123 milligrams weight loss.

EXAMPLE 8

The process of Example 1 was repeated except that the nonyl phenol was replaced by para-cresol.

The elemental analysis of the product showed it to contain 10.2 wt.% sulphur, 4.9 wt.% phosphorous, 0.8 wt.% chlorine, 70.7 wt.% carbon and 8.6 wt.% hydrogen and the molecular weight was 1187.

The theoretical content of the compound:

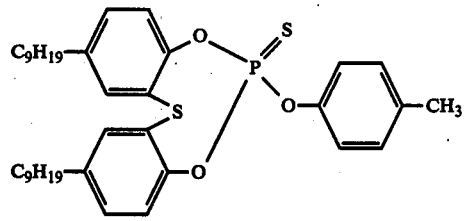

is 10.0 wt.% sulphur, 4.8 wt.% phosphorous, 61.9 wt.% carbon and 8.2 wt.% hydrogen with a molecular weight of 642 thus indicating the presence of polymeric molecules. The product was soluble in paraffinic mineral oils at amounts greater than 50 wt.%.

EXAMPLE 9

The process of Example 1 was repeated except that the nonyl phenol was replaced by dodecyl amine.

An oil solution containing 60 wt.% of the product was found to contain 2.4 wt.% phosphorous, 0.8 wt.% chlorine and 6.4 wt.% sulphur.

The theoretical content of a solution containing 60 wt.% of

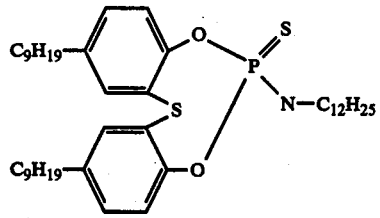

would be 2.8 wt.% phosphorous and 5.8 wt.% sulphur.

An oil containing 1.6 wt.% of the product was subjected to the Hertz 4 Ball test with the following results:

| Scar Diameter m.m. | 0.46 |
|---|---|
| Mean Load kg. | 42 |
| Seizure Load kg. | 100 |
| Weld Load kg. | 200 |

EXAMPLE 10

The process of Example 1 was repeated except that the nonyl phenol was replaced by

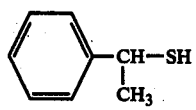

An oil solution containing 79 wt.% of the product contained 3.8 wt.% phosphorous and 8.5 wt.% sulphur.

The theoretical content of an oil containing 79 wt.% of:

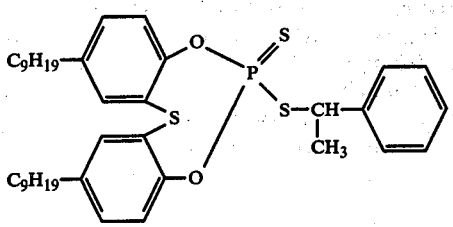

would be 4.0 wt.% phosphorous and 8.0 wt.% sulphur.

An oil containing 1.23 wt.% of this compound was subjected to the Hertz 4 ball wear test with the following results:

| Scar diameter mm | 0.26 |
|---|---|
| Mean Load kg. | 52 |
| Seizure Load kg. | 126 |
| Weld Load kg. | 200 |

EXAMPLE 11

The process of Example 1 was repeated except that the nonyl phenol was replaced by the compound:

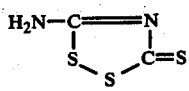

An oil solution containing 76 wt.% of the product contained 17.5 wt.% sulphur and 3.0 wt.% nitrogen.

The theoretical content for a solution containing 76 wt.% of the compound

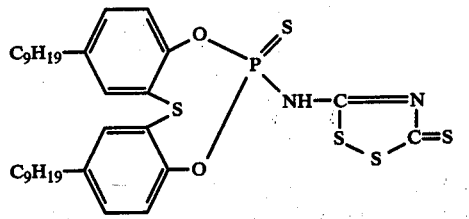

would be 17.8 wt.% sulphur and 3.1 wt.% nitrogen.

An oil solution containing 1.0 wt.% of this compound was subjected to the Hertz 4 Ball wear test with the following results:

| Mean Load kg. | 46 |
|---|---|
| Seizure Load kg. | 126 |
| Weld Load kg. | 200 |

EXAMPLE 12

The process of Example 1 was repeated by firstly replacing the nonyl phenol with trichloroethanol (A) and secondly with pentachlorphenol (B). Oil solutions containing 0.85 wt.% A, 2.0 wt.% A, 0.85 wt.% B and 2.0 wt.% B were subjected to the Hertz 4 Ball wear test with the following results:

|  | 0.85 wt. % A | 2.0 wt. % A | 0.85 wt. % B | 0.85 wt. % |
|---|---|---|---|---|
| Wear Scar mm | 0.74 | 0.50 | 0.45 | 0.50 |
| Mean Load kg | 41 | 51 | 40 | 56 |
| Seizure Load kg | 126 | 126 | 100 | 126 |
| Weld Load kg | 200 | 315 | 200 | 250 |

EXAMPLE 13

The process of Example 1 was used but the nonyl phenol sulphide was replaced by para-cresol sulphide.

Elemental analysis of this product showed it to contain 12.3 wt.% sulphur, 5.7 wt.% phosphorous, 0.5 wt.% chlorine, 66.4 wt.% carbon and 7.2 wt.% hydrogen and to have a molecular weight of 595. The theoretical content for the structure:

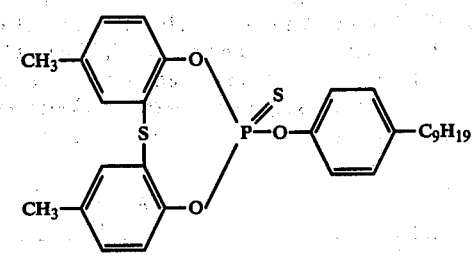

is 12.1 wt.% sulphur, 5.9 wt.% phosphorous, no chlorine, 66.1 wt.% carbon and 7.0 wt.% hydrogen with a molecular weight of 526. The product was soluble in an amount less than 2 wt.% in paraffinic mineral oil.

EXAMPLE 14

The process of Example 13 was repeated except that the nonyl-phenol was replaced by para-cresol. Elemental analysis of the product showed it to contain 15.8 wt.% sulphur, 7.3 wt.% phosphorous and 0.5 wt.% chlorine with a molecular weight of 416.

The theoretical content of the structure:

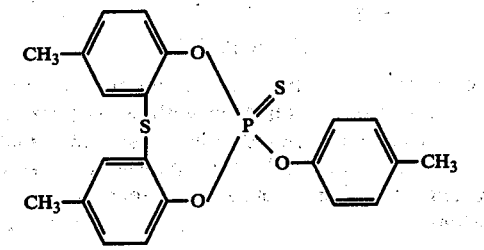

being 15.4 wt.% sulphur, 7.5 wt.% phosphorous and a molecular weight of 414. The product was soluble in an amount less than 2 wt.% in paraffinic mineral oil.

EXAMPLE 15

The process of Example 1 was repeated except that the nonyl phenol was replaced by thiophenol.

The product obtained was soluble in an amount less than 2 wt.% in paraffinic mineral oil.

EXAMPLE 16

The process of Example 15 was repeated except that the nonyl phenol was replaced by aniline. Here again the product obtained was soluble in an amount less than 2 wt.% in paraffinic mineral oil.

EXAMPLE 17

This Example demonstrates an alternative process to that of Example 1 for the preparation of products according to the invention.

671 grams of a 70 wt.% active ingredient nonyl phenol sulphide, 215 grams of a paraffinic mineral oil and 29 grams of flowers of sulphur were charged to a 2 liter vessel. With the temperature of the reactor at 60° C. 137.5 grams of phosphorous trichloride were added gradually.

When 78 grams of hydrochloric acid had been liberated 229 grams of nonyl phenol were introduced into the reactor whilst its temperature was at 128° C. and finally 22 grams of ethylamine added to ensure removal of all the hydrochloric acid and the amine hydrochloride removed by filtration.

Analysis of the product obtained showed it to be the same as the product of Example 1.

I claim:

1. Oil soluble compounds of the general formula:

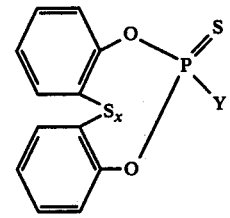

where Y is selected from the group consisting of phenoxy, alkylphenoxy and alkoxy, and x is 1 or 2; and compounds of said formula wherein either or both of the aromatic rings are substituted with an alkyl group of 2 to 25 carbon atoms.

2. A lubricating oil comprising from 99.99 to 90 wt.% of an oil and from 0.01 to 10 wt.% of a compound according to claim 1.

3. Compounds according to claim 1 in which the aromatic rings are substituted with an alkyl group containing from 2 to 25 carbon atoms.

4. Compounds according to claim 1 in which Y contains an aromatic ring which is substituted with an alkyl group containing from 2 to 24 carbon atoms.

5. Compounds according to claim 3 in which the alkyl groups are nonyl groups.

6. An additive concentrate comprising 95% to 60% by weight of an oil and 5% to 40% by weight of a compound according to claim 3.

7. A lubricating oil according to claim 2, wherein said aromatic rings are substituted with alkyl groups of about 6 to 15 carbon atoms.

8. A lubricating oil according to claim 7, wherein Y is phenoxy.

9. A lubricating oil according to claim 7, wherein Y is alkylphenoxy, and said alkyl portion of said alkylphenoxy contains 6 to 15 carbon atoms.

10. A lubricating oil according to claim 7, wherein Y is alkoxy.

* * * * *